US005765554A

United States Patent [19]

Somerson et al.

[11] Patent Number: 5,765,554

[45] Date of Patent: Jun. 16, 1998

[54] ALARM CONTROL SYSTEM FOR MEDICAL VENTILATOR

[75] Inventors: Steven K. Somerson, Madison; Kevin G. Tissot, Brooklyn; James R. Homuth, DeForest, all of Wis.

[73] Assignee: Ohmeda Inc., Liberty Corner, N.J.

[21] Appl. No.: 622,902

[22] Filed: Mar. 29, 1996

[51] Int. Cl.[6] ............................................. A61M 16/00
[52] U.S. Cl. ......................... 128/205.23; 128/204.18
[58] Field of Search ..................... 128/205.24, 205.23, 128/204.21, 204.24, 204.22, 204.25, 205.11, 204.18

[56] References Cited

U.S. PATENT DOCUMENTS

| | | | |
|---|---|---|---|
| 3,807,446 | 4/1974 | Driskell et al. | 128/205.24 |
| 4,323,064 | 4/1982 | Hoenig et al. | 128/205.24 |
| 5,315,989 | 5/1994 | Tobia | 128/204.28 |
| 5,474,062 | 12/1995 | DeVires et al. | 128/205.24 |

OTHER PUBLICATIONS

International Operation and Maintenance Manual—7800 Ventilator, Softwre revision 4.XX.

*Primary Examiner*—V. Millin
*Assistant Examiner*—William J. Deane, Jr.
*Attorney, Agent, or Firm*—Roger M. Rathbun; Salvatore P. Pace

[57] ABSTRACT

A control system where the clinician can have manual control of the state for various alarms, generally volume alarms and apnea alarms. The control is interactive, that is, while the clinician can manually set the state in a variety of settings, the control system automatically overrides the clinician's selection to activate both the volume and apnea alarms wherever the mechanical ventilator is turned on. In addition, there is another override where a breath is detected by the ventilator to turn all of the alarm systems from both being inactive to both alarms being active.

4 Claims, 2 Drawing Sheets

ALARM CONTROL SYSTEM FOR MEDICAL VENTILATOR

BACKGROUND OF THE INVENTION

This invention relates to medical ventilators and, more particularly, to an improved system for providing a smart selection system for determining various states of the apnea alarm and the volume monitoring of the system that provides interaction between user selection and automatic switching between those states.

In general, medical ventilators are used to provide respiratory support and anesthesia to patients undergoing medical treatment. The primary function of the ventilator is to maintain suitable pressure and flow of gases inspired and expired by the patient. Ventilators are used in the administration of anesthesia to a patient undergoing an operation and which may include a bellows arrangement or can be used in providing life support to a patient to provide the breathing function directly to that patient.

The gas is actually delivered to the patient from the ventilator through a patient circuit that is generally a disposable unit having one end coupled to the patient via a face mask or other administration device and the other end is connected to the ventilator. In general, such patient circuits include an inhalation limb that receives the gas from the ventilator to deliver that gas to the patient and an exhalation limb where the patient's exhalation gasses are conveyed away from the patient.

Among the normal monitoring functions of medical ventilators is the apnea alarm, that is, the alarm that signals to the user that breathing has ceased or has been reduced to an unacceptable level. That alarm is normally based on a flow sensor that may be located in the exhalation limb of the patient circuit and which must detect a perceptible flow from the patient within a predetermined period of time or the alarm is activated. The alarm system may utilize a single flow sensor in the exhalation limb or use more that one sensor.

Current apnea alarms are generally based in the monitoring of volume of gas exhaled from the patient and therefor monitor the flow in the patients exhalation by a flow sensor. That flow is then integrated with respect to time to obtain a determination of exhalation volume and the apnea alarm signals if that exhaled volume is not of a predetermined value, indicating that the patient is not properly exhaling.

As a further alarm system in such medical ventilators is the volume alarm and which may, again, rely upon a flow sensor located in the patient's exhalation limb. With this alarm, the clinician may set a high and low limit and the alarm will sound when the tidal volume of gas exhaled by the patient is outside of those established limits. Also relying on the same volume alarm system is an alarm based on minute volume, that is, the volume of gas delivered to the patient in a minute. That, again is an alarm for which the clinician sets certain high and low settings and the alarm will be activated if the minute volume is outside of either of those established limits.

As a further function of the monitoring system for a medical ventilator in the monitoring of apnea and volume in general, there is a selection process whereby the user can select the various states available for the apnea alarm and the normal volume monitoring of breaths to and from the patient. Certainly, the user can make a manual choice to have the apnea alarm in its functioning or active state whenever desired, however, there are times, such as during induction of the patient or when the clinician is manually bagging the patient, that the apnea alarm is not needed and may be a nuisance in causing an alarm condition when that condition is not warranted.

In such cases, the clinician may desire to disable the alarm. For example, during induction, the clinician is actively monitoring the patient and therefore does not need to rely upon an apnea alarm and, similarly, when the clinician is manually bagging the patient, the clinician is again actively watching over the patient conditions and the apnea alarm is not needed.

During mechanical ventilation, however, where the ventilator is carrying out the ventilation of the patient, the clinician may be preoccupied with other duties and it is important to have the apnea alarm activated so that any alarm condition can immediately be brought to the attention of the clinician.

In addition, during start up of the ventilator, the alarms are initially inactive and it is important to have the alarm conditions activated wherever the patient is attempting to breathe such that the detection of the breath will cause the system_to move from the position where no alarms are activated to the condition where_both alarms are activated for the safety of the patient.

Accordingly, it would be advantageous for the clinician to have certain control over the various states of the apnea alarm as well as the volume monitor alarms, but provide some smart safeguards that are carried out by the control system automatically to change the manually selected state of those monitoring functions where needed to protect the patient.

SUMMARY OF THE INVENTION

In accordance with the present invention, a system is provided that allows the clinician to carry out the selection of the various states of the apnea alarm and the volume monitoring alarms and which is interactive with other sensed parameters. For example, in the preferred embodiment, the user may select any_one of four states of the alarm systems, that is, a state where both alarms are_inactivated, a state where both alarms are activated, a state where the apnea alarm is activated but the volume alarm inactivated and finally, a state where the apnea alarm is inactivated but the volume alarms are activated.

But even though the user can initially select the desired preference, there are overriding functions that respond to outside parameters to automatically move the system state to another state. As an example, where the apnea and volume_alarms are initially inactive, when the system senses the breathing of the patient, the state of both of the alarms, i.e. apnea and volume alarms is automatically moved to the active state.

Similarly, in any state selected, the activation of the mechanical ventilator will automatically put the state of both the apnea and volume alarms into the active state overriding the choice of the clinician.

Accordingly, the system allows the clinician to select between various states of the apnea alarm and the volume monitor, however, there is also a smart input that will automatically, without user intervention, shift the apnea alarm and volume monitoring system to the proper state as added protection to the patient and assure the clinician that the proper state of that alarm and monitor is being utilized.

Other objects, features and advantages of the present invention will be more readily apparent from the detailed description of the preferred embodiment set forth below, taken in conjunction with the accompanying drawings.

DESCRIPTION OF THE PREFERRED EMBODIMENT

Figure 1:
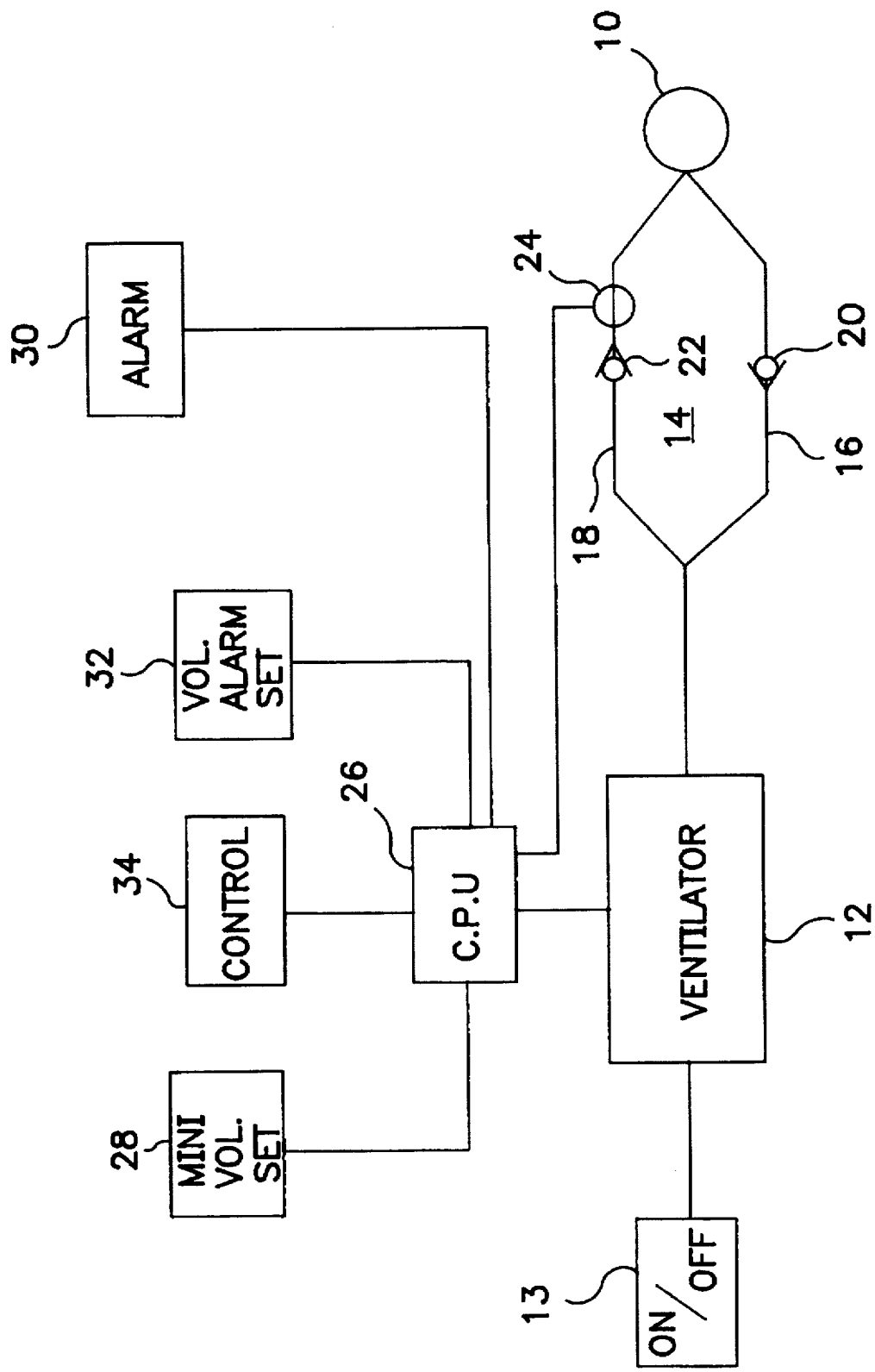
FIG. 1 is a block diagram of the overall ventilator system that may be used with the present invention.

Referring now to FIG. 1, there is shown a schematic view of a ventilator apparatus suitable for carrying out the present invention. In FIG. 1, there is shown a typical system for carrying out the ventilation of a patient 10 including a ventilator 12. The ventilator 12 may be of conventional construction or may be constructed as shown and described in U.S. Pat. No. 5,315,989 of Tobia, assigned to the present assignee and the disclosure of which is incorporated herein by reference.

As is conventional, the ventilator 12 provides a breathing gas to the patient 10 by means of a patient breathing circuit 14 which comprises, preferably, an inhalation limb 16 and an exhalation limb 18. Appropriate check valves 20 and 22 are provided in the inhalation limb 16 and the exhalation limb 18, respectively, to insure that the gas flows in the proper direction through the patient circuit.

The patient 10 is connected to the patient breathing circuit 14 by means of a connector, such as a Y piece. A flow sensor 24 is provided in the exhalation limb 18 of the patient breathing circuit 14 and its purpose will be later explained. It is also noted that while the present invention is described in terms of a single flow sensor located in the exhalation limb 18, the invention may be used with two flow sensors, one located in the exhalation limb 18 and the other located in the inhalation limb 16.

Ventilator 12 is controlled by a processor, shown as a central processor unit or CPU 26 and which provides the input to the ventilator 12 to carry out its various functions, again, in conventional manner. the ventilator 12 may be activated by the user by a switch 13 where the ventilator provides a breath automatically to the patient or inactivated when the clinician is manually bagging the patient and thus is providing the breath to the patient by squeezing a flexible bag to provide that breath.

As typical controls that are inputted to the CPU 26 various alarm conditions are set by the clinician and which establish the alarm conditions for certain functions of the ventilator. As shown, one alarm is the minute volume alarm and the minute volume input 28 allows the user to determine the alarm limits for that parameter. For example, the minute volume is a measure of the amount of gas delivered to the patient in a minute and may range from about 0.1 to 30 liters per minute. Therefore, the clinician may set a minimum value and a maximum value for that parameter and an alarm 30 is activated when the flow sensor 24 detects that parameter. For minute volume, the flow sensor 24 determines the flow in the exhalation limb 18 and that value is calculated with respect to a clock it the CPU 26 to provide a timed signal representative of the volume per minute seen by the sensor 24.

A further alarm that is normally available on medical ventilators is the volume alarm, that is based upon the volume that is exhaled by the patient.

That volume must be a least a predetermined volume or an alarm will sound.

In the case of the volume alarm, again the flow sensor 24 may be used and the signal from the flow sensor 24 is integrated with respect to time in the CPU 26 to obtain a signal representative of volume. This alarm, like the minute volume alarm is satiable by an input 32 that is determined by the user to be within, for example 20 to 1600 ml.

Generically, the minute volume and the volume parameters are considered as volume monitors and their control state may generally be selected by the clinician together as will later be explained.

Lastly, there is a standard monitor or alarm known as the apnea alarm and it again depends on signals from the flow sensor 24 to provide an input for the alarm function. With the apnea alarm, the flow sensor 24 must see a certain discernable flow which is integrated to volume. A certain volume must be seen during a predetermined time period to continually reset the alarm. As an example, the alarm may reset if the flow is seen by the flow sensor 24 every thirty seconds and, conversely, if the flow is not sensed by the flow sensor 24 during that period of time the alarm 30 will be activated to bring that condition to the attention of the clinician.

The selection of what alarms are active or inactive is made by the clinician in accordance with personal preferences, the condition of the patient or the operation of the ventilator. Therefore, depending on the particular situation, the apnea alarm may be on or off and the volume alarms may be on or off and thus their state is subject to the selection by the clinician with certain automatic operation as will be explained. As shown in FIG. 1, the control panel 34 enables the clinician to select the desired state of the alarms and the signal from the control panel 34 is communicated to the CPU 26.

Figure 2:
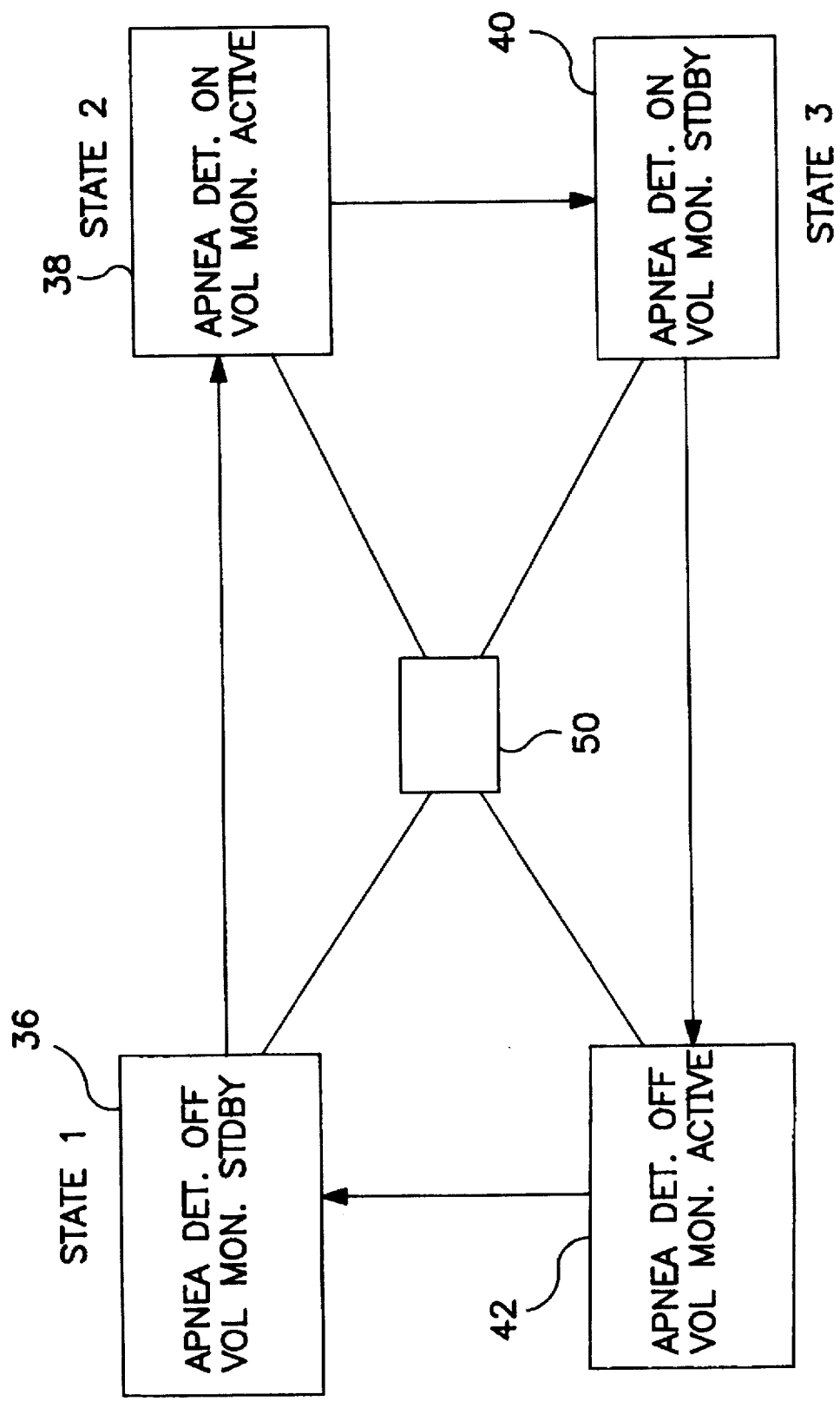
FIG. 2 is a schematic view illustrating the various alarm states of the preferred embodiment of the present invention.

Turning now to FIG. 2, there is shown a schematic view of the states of the various alarms on control panel 34 that is utilized by the clinician to make a selection of the various states of the alarm systems. The control panel 34 is, of course, merely schematic to represent the various states of the alarm system and may be carried out in many ways. The states may actually be shown on a panel by a lighted portions of the panel or any other means may be employed to let the user know what state is current of the alarms.

Basically, however, there are four alarm states represented by the block 35 as state 1, block 38 as state 2, block 40 as state 3 and block 42 as state 4. Each of the states is unique. For example, state 1, block 36 is the state where the apnea detector alarm is off and the volume monitor alarms are on standby, thereby not activated. In state 2, block 38 both the apnea alarm and the volume alarms are active, state 3, block 40, the apnea alarm is on and the volume monitor in standby and finally in state 4, block 42, the apnea detection alarm is off and the volume alarm is active.

The user can select any one of the states by, for example, depressing a button 50 to advance the state to the next succeeding state, that is, by depressing the button 50, the state will advance from state 1 to state 2 and successively thereafter. Therefore, the user can select whatever alarm the clinician desires to be operative and/or inoperative. Obviously, the selection of the particular state is by conventional means and can be a selector switch or other device to advance the state to the next succeeding state.

Taking, therefore, the states in order, in state 1, none of the alarms is in the active state. Therefore state 1 is intended for use as the ventilator is started up since, at the start up, the mechanical ventilator is not activated until it is enabled by the clinician. Therefore, the ventilator alarm system is initially in state 1 but will automatically change to state 2 if any breath is observed by the flow sensor, since patient breathing has commenced. In addition, the control panel will also immediately switch to state 2 upon the clinician activating the mechanical ventilation by ventilator 12 via switch 13.

Accordingly while the clinician can always manually activate the control from state 1 to state 2, it will, on its own, make the switch without the intervention of the clinician if a breath is detected or the ventilator 12 is activated to commence mechanical ventilation. In either condition, it is important at that time that the patient have full monitoring and all alarms are thus activated when the mechanical ventilator 12 is on and will remain in state 2 for so long as the ventilator is on. State 2, therefore is the most vigilant state since all of the relevant alarms are active.

At this point, the clinician may activate the button 50 to change the state to state 3 providing mechanical ventilation is again deactivated. In state 3, the clinician may be bagging the patient or the patient may be carrying out spontaneous breathing during emergence from anesthesia. The clinician may want apnea detection, however, in this state, the volume monitors will be seeing erratic breathing and the clinician may not want to have constant alarms where that breathing is outside the limits set in the CPU 26.

In state 4, therefore, again the mechanical ventilator 12 must be inactive and the apnea alarm is off and the volume alarms are activated. In this state, the clinician typically will set the alarm limits to their most remote settings, that is the highest alarm setting of the high setting and the lowest alarm setting of the low alarm setting such that the volume alarms are basically out of the system. Here, the clinician may be bagging or intubating the patient. In effect, the alarm conditions are generally set by the clinician to be similar to the state 1 conditions and all of the alarms are inactivated, however, the control will stay in state 4 even if spontaneous breathing is detected, unlike state 1 where the detection of breaths would automatically cause the control scheme to advance to the state 2 position.

It should be pointed out, however, whenever the ventilator 12 is put in the on position and activated, the control will automatically go to the state 2 condition such that all of the various alarms are activated no matter what state the control panel is in when that activation of the ventilator 12 takes place.

Accordingly the control system is activated by the user to choose the particular alarm desired for the volume and apnea alarms, however, it also overrides the clinician's selection to activate all of the alarms when the ventilator 12 is activated for the safety of the patient and to insure that there is the maximum of alarm protection where the patient is undergoing mechanical ventilation.

While the present invention has been set forth in terms of a specific embodiment, it will be understood that the alarm control system algorithm herein disclosed may be modified or altered by those skilled in the art to other configurations. Accordingly, the invention is to be broadly construed and limited only by the scope and spirit of the claims appended hereto.

We claim:

1. An alarm system for a medical ventilator providing a breath to a patient and receiving exhaled breath from a patient, said alarm system comprising a mechanical ventilator, said ventilator having a selector means to activate said ventilator to provide mechanical ventilation to a patient and to deactivate said ventilator, a volume alarm for detecting the volume of gas exhaled by a patient, said volume alarm having an activated status and a deactivated status, an apnea alarm for providing an alarm when insufficient volume has been exhaled by a patient within a predetermined time period, said apnea alarm having an activated status and an inactivated status, control means operable by a user to select any one of a plurality of states of active and or inactive status of said volume alarm and said apnea alarm, one of said states being where said apnea alarm and said volume alarm are both active, and means responsive to the activation of said ventilator by said selector means to override said selected state by a user to immediately select said state wherein said apnea alarm and said volume alarm are both activated.

2. An alarm system for a medical ventilator as defined in claim 1 wherein said control means is operable to select any one of four states.

3. An alarm system for a medical ventilator as defined in claim 1 wherein one of said states comprises said apnea alarm and said volume alarm both being in the inactive state.

4. An alarm system for a medical ventilator as defined in claim 3 wherein said ventilator comprises a sensor to detect the patient's breath to immediately cause said control means to move from said state where said apnea and volume alarms are inactive to the state wherein both said apnea alarm and said volume alarm are active.

* * * * *